United States Patent [19]

Terminiello et al.

[11] 4,338,982
[45] Jul. 13, 1982

[54] ROTATING RIFFLER

[75] Inventors: Michael A. Terminiello, Carmel, Ind.; Stanley E. Gebura, Mountain Lakes, N.J.

[73] Assignee: BASF Wyandotte Corporation, Wyandotte, Mich.

[21] Appl. No.: 209,612

[22] Filed: Nov. 24, 1980

[51] Int. Cl.³ .............................................. B65B 43/56
[52] U.S. Cl. ................................... 141/132; 141/131; 141/177
[58] Field of Search .................. 211/77, 129; 248/315, 248/558, DIG. 12; 141/102, 131–133, 177, 324

[56] References Cited

U.S. PATENT DOCUMENTS

| 915,725 | 3/1909 | Baines et al. | 141/177 X |
| 2,055,075 | 9/1936 | Gardner | 141/133 |
| 2,441,774 | 5/1948 | Shaw et al. | 141/131 |
| 3,667,512 | 6/1972 | Jackson | 141/131 X |

Primary Examiner—Frederick R. Schmidt
Attorney, Agent, or Firm—Norbert M. Lisicki

[57] ABSTRACT

A rotating riffler for the purpose of withdrawing smaller laboratory-sized representative particulate samples from larger samples. This comprises a rotating disk having an interchangeable top plate of plastic foam having openings therein to accommodate sample containers. Where different size sample containers are employed, the plastic foam plate is changed to accommodate them. The rotating disk is mounted on a base containing a variable speed drive and is supported at the periphery by bearings rather than by the shaft. A slurry or dry volume of particles of which a smaller representative sample is required, is fed into a funnel-like device, then drops in a controlled flow into the sampling containers rotating below the funnel. "V"-shaped bridging devices having curved legs are attached between each pair of containers to prevent spilling.

14 Claims, 4 Drawing Figures

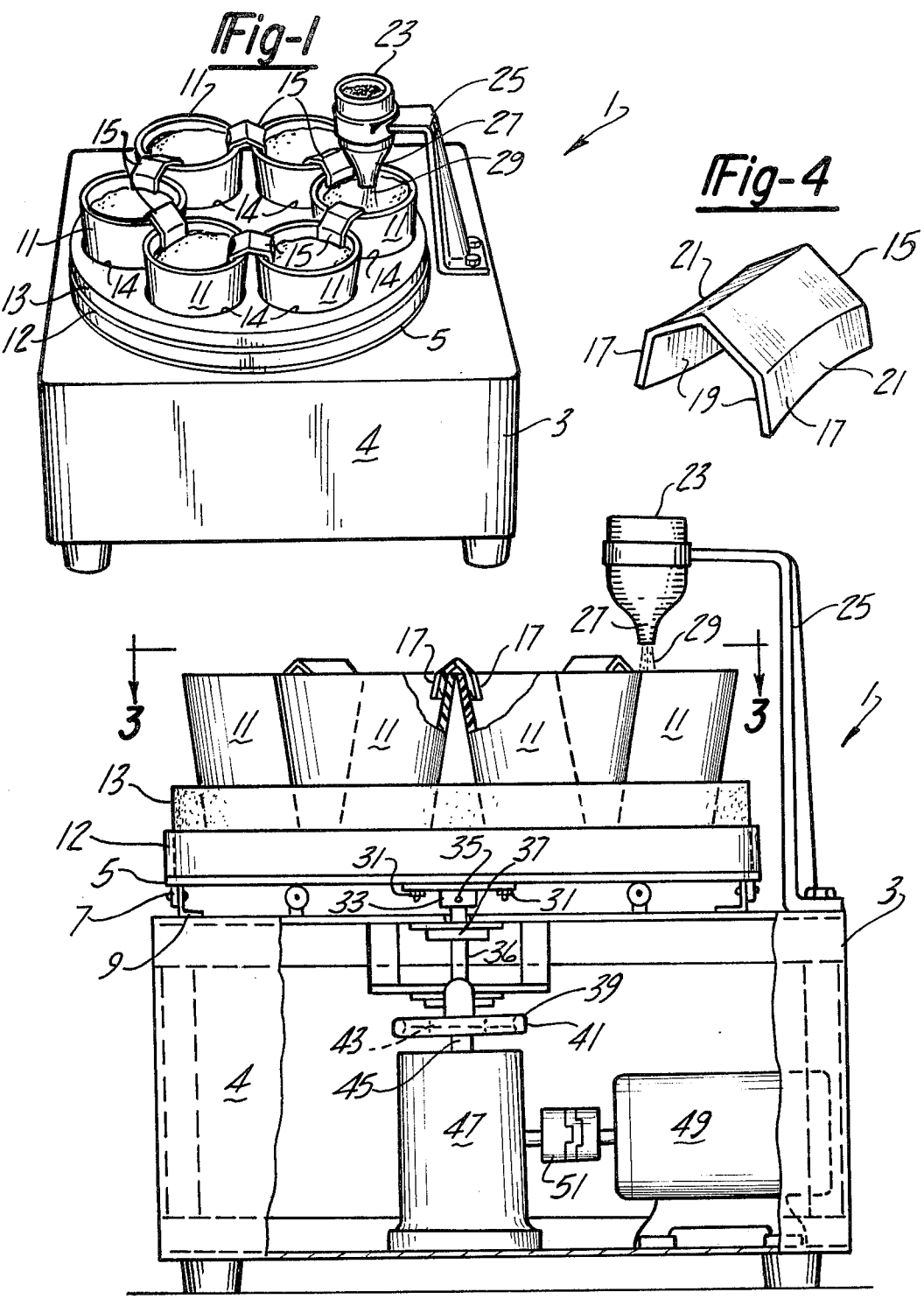

ROTATING RIFFLER

BACKGROUND OF THE INVENTION

1. Field of the Invention

The present invention relates to sampling devices for obtaining representative samples from a bulk quantity of material.

2. Description of the Prior Art

Particulate materials used in a process often at some time or another must be withdrawn from a larger mass of material. The sample withdrawn may be used in the actual process or may be used for analysis as a control. Wherever it is assumed that the sample is the same, or representative of the bulk material, that sample must be obtained in a statistically valid manner.

It is difficult to obtain a representative sample of material from a bulk quantity of a mixture of particles in a fluid. If the mixture is freely flowing like dry sand in air, the large particles tend to separate from the small ones and locate at one or more boundaries within the mixture. In the case of cohesive materials, like cornstarch or viscous pastes, it is difficult to cause the material to flow so that sampling from the entire mixture is impossible.

Many techniques have been proposed and are being used for sampling powders and suspensions. In the simplest technique, a sample of powder or suspension is removed from the exposed surface of the bulk material, using a scoop or similar receiver. This method gives samples which have been taken from the outer areas of the material and are thus liable to be non-representative of the bulk. The technique is used extensively since it is rapid and inexpensive, but it is unsuitable for freely flowing powder since these roll off the scoop.

Many more complex sampling techniques have been devised, all of which have some disadvantages. An extensive study of sampling devices indicates that the spinning riffler is very efficient. This device consists of a ring of containers rotating under a powder feed so that each time a container passes under the stream of powder, it collects a small portion. The sample in each container will thus be made up of many small portions drawn from all points of the bulk. A temporary spinning riffler can be constructed simply with a phonograph turntable, a supply of paper cups in close proximity to the periphery of the turntable with a funnel or hopper positioned above the ring of paper cups. Such a device is disclosed in the article "Determining the Characteristics of Fine Powders", by Brian H. Kaye. pages 239 and 240 of *Chemical Engineering* for November 7, 1966.

In U.S. Pat. No. 797,144, a sampler or rotating riffler is disclosed which employs a horizontal rotating disk with sample containers supported thereby which is mounted on a base containing a drive. A volume of particles is fed into a funnel-like device wherby it drops in a controlled flow into the sampling containers rotating below the funnel.

In U.S. Pat. No. 2,441,774, a rotating riffler type device is disclosed which employs a rotatable assembly driven by a variable speed drive. The volume of particles is fed into a funnel-like device from which they drop in a controlled flow into sampling containers rotating below the funnel. The rotatable support for the sampling containers is a ring which is supported from above by tie rods. Antispill devices are provided between the sampling containers.

In U.S. Pat. No. 3,215,173, a bag-filling device is disclosed which rotates and has a series of funnels around the periphery of a round upper portion which are fed from a conveyor belt as the apparatus rotates. Below these funnels is a space for attaching bags which rest on weighing devices, and the entire apparatus is supported by peripheral bearings. However, this apparatus is not a riffler for samples but rather a device for filling bags which move one at a time under the conveyor belt rather than rapidly rotating to get a representative sample.

In U.S. Pat. No. 3,667,512, a sampling device is disclosed for obtaining representative samples of materials from a bulk quantity thereof which includes a plurality of rotating sample containers which are sequentially and repetitively fed by a flow stream of the material which emanates from a hopper. A screw conveyor mechanism controls the flow rate of the stream to insure representativeness and statistical validity of the samples.

The rotating riffler type devices described above are substantial improvement over the other prior art devices. However, a need exists for sampling means which can be used both in the case of extremely free-flowing materials or highly cohesive materials to get a sample which is statistically valid and identical in composition to the original batch. More specifically, the devices described above represent a problem if the containers are merely loosely placed upon a disk such as the use of paper cups on a phonograph turntable. With such devices, if the disk is rotated rapidly enough, which may be necessary with some materials, the paper cups would fly off the disk. Accordingly, some means is generally needed to retain the containers on the disk and the prior art devices for this purpose generally are adapted for only one size of container. If the riffler is to be used for a variety of materials, it is often necessary to employ a variety of containers and devices providing for variety of size and shape of containers.

Also, in general the disk or similar member is mounted on a single shaft. Generally due to flexibility of the disk and shaft and/or inaccurate mounting of the disk on the shaft which serves both the function of rotating and supporting this disk, the disk will not remain level but will flex due to a cantilever effect. Such flexing can result in uneven distribution of samples among the cups or the containers. In addition, with the prior art devices, considerable material is wasted and lost, particularly where the containers are round in cross-section, by spill-over as the cups pass beneath the discharge from the hopper or funnel.

Accordingly, it is the purpose of the instant invention to provide an apparatus for obtaining a representative sample of material from a larger batch or bulk of the material which is free from the above deficiencies.

SUMMARY OF THE INVENTION

In overcoming the above deficiencies, the sampling device of the present invention comprises a revolvable first disk and individual readily portable containers resting upon said disk. The containers are positioned in close proximity to the periphery of the disk and are so placed that their upper edges are adjacent and generally touching one another whereby they form a ring around the disk. The containers are held in position and prevented from flying off the disk by the use of a second disk which rests upon the first disk and has openings defined therein of such size and shape as to closely fit the outside of the containers when the containers rest upon the first disk. The second disk may simply rest upon the first disk and be easily removed therefrom whereby, in the event different sized containers are desired, the containers and the disk may be removd and a different disk and set of containers placed on the first disk in the same manner. Each additional second disk is provided with suitable openings to closely fit the outside of an additional set of containers. Where a large variety of materials are to be sampled using a riffler of this type, a plurality of sets of containers and a plurality of sets of plastic foam disks corresponding to the size respectively of the containers in each set may be employed and the proper set of containers and plastic foam disks may be employed according to the characteristics of the material to be sampled.

A hopper for the bulk quantity of material being provided with a suitable discharge opening is positioned over the path of travel of the containers and supported by conventional support means. Thus, a flowing stream of the bulk material may be discharged from the hopper into the containers supported on said disk. Means are provided to rotate the first disk thereby sequentially and repeatedly moving the containers individually into intercepting relation with the flow stream.

The main support for the first disk is provided by a set of bearings positioned closely adjacent to the periphery of the first disk which is in turn supported by suitable structural means so that the main support is by such bearings. Rotation is imparted to the disk by a shaft affixed to the center of said disk and driven by suitable means such as a prime mover which may employ a variable speed drive.

In a preferred embodiment of this invention, the containers are round in cross-section and bridging means are provided extending from the inner wall of one container to the inner wall of the next container. These are generally a plurality of "V"-shaped baffles, the legs, at least the lowe portion of the legs of the "V", being curved to fit within said containers. That is to say the legs are curved such that the surfaces of the curved legs facing each other are convex and generally speaking, the opposite face of each leg would then be concave.

BRIEF DESCRIPTION OF THE DRAWINGS

FIG. 1 is a three dimensional view of the rotating riffler apparatus of the instant invention;

FIG. 2 is a side elevational view of the rotating riffler of FIG. 1, wherein portions of the frame and housing are removed for purposes of clarity;

FIG. 4 is a three dimensional view of the antispill bridge for use between the containers of the rotating riffler.

DETAILED DESCRIPTION OF THE PREFERRED EMBODIMENT

Figure 3:
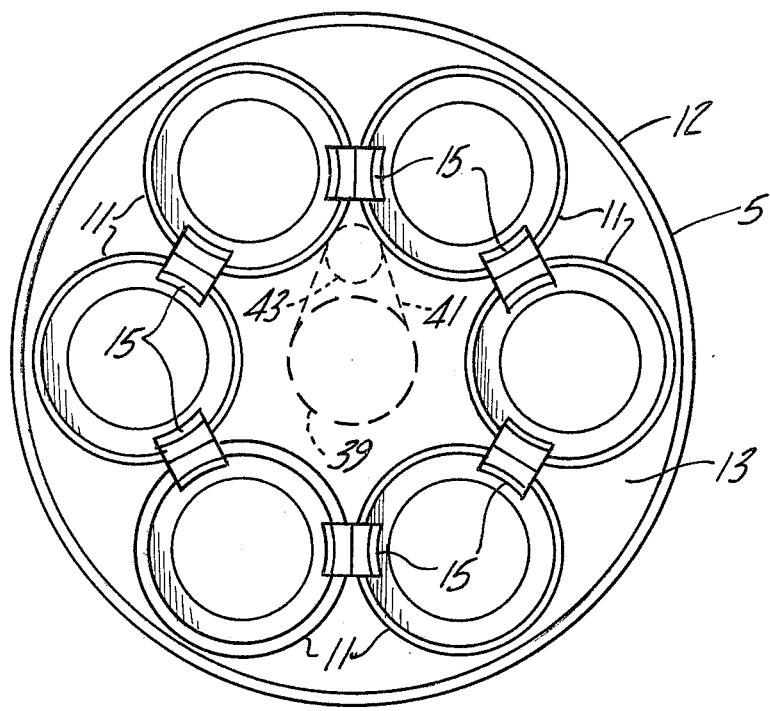
FIG. 3 is a top view of the rotating riffler taken along the line 3—3 of FIG. 2.

With reference now to the drawings and more particularly to FIGS. 1 and 2 thereof, a sampling device indicated generally at 1 in accordance with the present invention, is shown to comprise a suitable support structure 3, covered by a suitable housing 4, and a revolvable disk 5 mounted on said structure 3. Disk 5 and support structure 3 may be fabricated of any suitable rigid material such as steel. Disk 5 is supported by means of peripheral bearings 7 mounted on suitable mounting members 9 which in turn are mounted on support structure 3. Containers 11, which preferably are round in cross-section and may have tapered side walls, rest upon disk 5 in close proximity to the periphery thereof. There are a sufficient number of said containers 11 whereby, when properly placed, their upper edges are adjacent to one another. A second disk 13 of plastic form material, shown more clearly in FIG. 3, having a diameter slightly less than that of disk 5, rests upon the first disk 5 by gravity and is therefore easily removable therefrom. Disk 13 may be manufactured from any suitable plastic foam material. However, polystyrene foam is preferred while polyurethane foam may also be employed. Other foam materials such as polyethylene foam and even foam rubber, both natural and synthetic, may also be employed. Disk 13 has openings 14 defined therein of such size and shape as to closely fit the outside of the containers 11 when the containers rest upon disk 3.

In order to maintain disk 13 in place on disk 5, a ring member 12 of suitable material such as steel is affixed to disk 5 by suitable means such as welding. Preferably the outside diameter of ring 12 is the same as that of disk 5. The inside diameter of ring 12 is slightly larger than that of disk 13 such as to provide a snug fit but large enough to permit easy removal of disk 13.

"V"-shaped antispill or bridging devices, indicated at 15 and shown more clearly in FIG. 4, having curved legs 17 attached to or integral with the "V" portion of device 15, are provided between each pair of containers 11 in such a manner that they extend from the inner wall of one container to the inner wall of the next container. Said curved legs 17 are curved to fit the inside of the containers, i.e., have the same curvature thereof. Thus, the surfaces 19 of said legs 17 facing each other are convex with the opposite surfaces 21 thereof generally being concave and having generally the same curvature as or parallel to, the surface 19.

An important feature of the instant invention lies in the fact that the disk 13 and set of containers 11 may be removed from the disk 5 and replaced by a different disk 13 and set of containers 11. The additional plastic foam disk has openings defined therein to closely fit the additional set of containers. In order to have an apparatus which is useful for sampling many different materials having different particle sizes and properties, several sets of containers 11 and disks 13 may be provided, each of which is interchangeable with the others depending upon the material to be sampled.

The bulk material or mixture to be sampled is contained within a supply hopper or funnel 23, which is supported by a suitable support structure 25 which most conveniently may be mounted on structure 3. The hopper or funnel 23 is mounted in elevated relation to the disks 5 and 13 and containers 11. Said hopper or funnel 23 is generally provided with a discharge nozzle 27 located over the path of travel of containers 11 for discharging a flow stream 29 of the material to said containers.

Means are provided to rotate said first disk thereby sequentially and repetitively moving the containers 11 individually into intercepting relation with the flow stream 29. Thus, each sample container 11 intermittently receives material which is only a portion of a sample from the bulk quantity in hopper or funnel 23 so that a sample is built up in each of said sample containers over a period of time after repetitive movement of the sample containers 11 into intercepting relation with the flow stream 29.

The means to rotate disk 5 comprises a hub 33 secured to the lower surface of disk 5, at the center thereof, by suitable means such as bolt and nut assemblies 31.

Mounted within hub 33, axially therewith and maintained in position by suitable means such as a set screw 35, is a vertical shaft 36. The shaft 36 is mounted on support structure 3 by means of a suitable bearing means 37 suitably affixed to structure 3. A "V"-belt pulley 39 is mounted on the lower end of shaft 36 and is driven by a "V"-belt 41 which in turn is driven by a pulley 43 mounted on a shaft 45 of a variable speed drive 47. Variable speed drive 47 is suitably mounted by conventional means on supoprt structure 3 and is driven by a conventional prime mover such as an electric motor 49 through a coupling 51.

The apparatus of this invention is equally applicable to slurries or dry volume particles where a smaller representative sample is desired from a larger sample. Certain types of dry materials may have a tendency to bridge or stick together and in such instances, agitating devices may be provided to allow continued free flow. Suitable devices which may be employed include augers and vibrators.

While preferred constructional features of the invention are embodied in the structure illustrated herein, it is to be understood that changes and variations may be made by those skilled in the art without departing from the spirit and scope of the appended claims.

What is claimed is:

1. An apparatus for obtaining representative samples of material from a bulk quantity thereof comprising a revolvable first disk, individual readily portable containers resting upon said disk in close proximity to the periphery thereof, and so placed that their upper edges are adjacent to one another; a second disk resting upon said first disk, a ring member affixed to said first disk having an inside diameter slightly larger than that of said second disk such as to provide a snug fit and permit easy removal of said second disk, said second disk having openings defined therein of such size and shape as to closely fit the outside of said containers when said containers rest upon said first disk, said containers being replaceable by at least one different set of containers and said second disk being replaceable by at least one other disk having openings defined therein to closely fit said additional set of containers; a hopper for said bulk quantity of material provided with a discharge opening located over the path of travel of said containers for discharging a flow stream of the material thereinto; means to rotate said first disk thereby sequentially and repetitively moving said containers individually into intercepting relation with said flow stream whereby said sample containers each intermittently receives material which is only a portion of a sample from the bulk quantity so that a sample is built up in each of said sample containers over a period of time after repetitive movement of said sample containers into said intercepting relation with said flow stream.

2. The apparatus of claim 1 wherein said second disk is made of plastic foam.

3. The apparatus of claim 2 wherein said plastic foam is polystyrene.

4. The apparatus of claim 2 wherein said plastic foam is polyurethane.

5. The apparatus of claim 2 wherein said first disk is supported by peripheral bearings.

6. The apparatus of claim 5 wherein said plastic foam is polystyrene foam.

7. The apparatus of claim 6 wherein said containers are round in cross-section.

8. The apparatus of claim 7 including "V"-shaped bridging means having curved leg portions attached thereto extending from the inner wall of one container to the inner wall of the next container, the curvature of said leg portions being convex on the sides thereof facing each other and having a curvature to match the curvature of the inside of said containers.

9. The appartus of claim 8 including agitating means within said hopper.

10. The appartus of claim 9 wherein said agitating means is an auger.

11. The appartus of claim 9 wherein said agitating means is a vibrator.

12. The apparatus of claim 9 wherein said first disk is rotated by the rotation of an axial shaft and a prime mover.

13. The apparatus of claim 12 wherein said first disk is rotated by the means of a shaft affixed to the center on the bottom of said disk and said shaft is rotated by a prime mover through a variable speed drive.

14. The apparatus of claim 13 wherein said prime mover is an electric motor.

* * * * *